(12) United States Patent
Chegou et al.

(10) Patent No.: US 12,188,946 B2
(45) Date of Patent: Jan. 7, 2025

(54) BIOMARKERS FOR DIAGNOSING TUBERCULOUS MENINGITIS

(71) Applicant: STELLENBOSCH UNIVERSITY, Stellenbosch (ZA)

(72) Inventors: Novel Njweipi Chegou, Bellville (ZA); Regan Shane Solomons, Kuils River (ZA); Gerhard Walzl, Cape Town (ZA); Masilo Charles Manyelo, Parow Valley (ZA)

(73) Assignee: STELLENBOSCH UNIVERSITY, Stellenbosch (ZA)

( * ) Notice: Subject to any disclaimer, the term of this patent is extended or adjusted under 35 U.S.C. 154(b) by 1037 days.

(21) Appl. No.: 17/057,628

(22) PCT Filed: May 23, 2019

(86) PCT No.: PCT/IB2019/054259
§ 371 (c)(1),
(2) Date: Nov. 20, 2020

(87) PCT Pub. No.: WO2019/224755
PCT Pub. Date: Nov. 28, 2019

(65) Prior Publication Data
US 2021/0199668 A1    Jul. 1, 2021

(30) Foreign Application Priority Data
May 23, 2018   (ZA) ................................ 2018/03410

(51) Int. Cl.
| | |
|---|---|
| *C12Q 1/70* | (2006.01) |
| *G01N 33/68* | (2006.01) |
| *A61B 5/15* | (2006.01) |
| *A61B 10/00* | (2006.01) |
| *G01N 21/64* | (2006.01) |

(52) U.S. Cl.
CPC ............ *G01N 33/6863* (2013.01); *A61B 5/15* (2013.01); *A61B 2010/0077* (2013.01); *A61B 2503/06* (2013.01); *G01N 2021/6439* (2013.01); *G01N 2333/35* (2013.01)

(58) Field of Classification Search
None
See application file for complete search history.

(56) References Cited

FOREIGN PATENT DOCUMENTS

| WO | WO2010070581 | 6/2010 |
|---|---|---|
| WO | WO2015159239 | 10/2015 |
| WO | WO2017058827 | 4/2017 |

OTHER PUBLICATIONS

Manyelo (Biomarkers, 2022, 27: 6, 549-561) (Year: 2022).*
International Search Report dated Jul. 26, 2019 in PCT Application No. PCT/IB2019/054259.
Manyelo et al., "Application of Cerebrospinal Fluid Host Protein Biosignatures in the Diagnosis of Tuberculous Meningitis in Children from a High Burden Setting," Mediators of Inflammation 2019, in 11 pages.
Tai, "Tuberculous Meningitis: Diagnostic and Radiological Features, Pathogenesis and Biomarkers," Neuroscience & Medicine 2013, 4, 101-107.

* cited by examiner

*Primary Examiner* — Celine X Qian
(74) *Attorney, Agent, or Firm* — Dickinson Wright PLLC

(57) ABSTRACT

Methods, devices, kits and computer-implemented methods for diagnosing (and optionally treating) tuberculous meningitis (TBM) are provided. In one embodiment, the method comprises testing a cerebrospinal fluid (CSF) sample from a subject suspected of having TBM for the presence of MPO and at least two other biomarkers, at least one of the other biomarkers being selected from the group consisting of IFN-γ, sICAM-1, VEGF-A and CXCL8. For example, the method can comprise testing the sample for MPO, IFN-γ and VEGF-A or for MPO, IFN-γ, sICAM-1 and CXCL8. In another embodiment, the method comprises testing a blood sample from a subject suspected of having TBM for the presence of at least one biomarker selected from the group consisting of adipsin (complement factor D), Ab42 and IL-10, and at least two other biomarkers. In one example, the method comprises testing the sample for the presence of adipsin (complement factor D), Ab42 and EL-10.

8 Claims, 7 Drawing Sheets

BIOMARKERS FOR DIAGNOSING TUBERCULOUS MENINGITIS

RELATED APPLICATIONS

The present application is a U.S. national phase application under 35 U.S.C. § 371 of International Application No. PCT/IB2019/054259, filed on May 23, 2019, and published on Nov. 28, 2019; which claims the priority of ZA Application No. 2018/03410, filed on May 23, 2018. The content of each of these related applications is hereby incorporated by reference in its entirety.

FIELD OF THE INVENTION

The invention relates to a method for diagnosing tuberculous meningitis in a subject, the method comprising detecting levels of specific biomarkers in a biological sample from the subject.

BACKGROUND TO THE INVENTION

Tuberculosis (TB) is currently the ninth leading cause of death worldwide and is the leading cause of death from a single infectious agent, *Mycobacterium tuberculosis* (MTB). About 10.4 million people were reported to have fallen ill with TB disease, with 1.7 million deaths reported in 2016. Seven countries including South Africa, Nigeria, India, China, Indonesia, Philippines and Pakistan contributed to 64% of the world's total burden of TB in 2016. In the same year, one million children were estimated to have become ill with TB disease, even though it is difficult to accurately estimate the burden of the disease in this population.

Sputum smear microscopy, the most widely used diagnostic test for TB, especially in resource-poor settings, has poor sensitivity, whereas the gold standard test (culture) has a long turnaround time (up to 42 days), is expensive, prone to contamination and requires extensive laboratory infrastructure, which is not often available in resource limited settings. The GeneXpert MTB/RIF Test®, arguably the most important recent advance in TB diagnosis, yields results within 2 hours and detects resistance to rifampicin as a proxy for MDR-TB diagnosis. However, despite the extensive roll out of GeneXpert, cost effectiveness and the requirement for technical infrastructure limits its use in resource-poor settings. As a consequence, the test is mostly offered in centralized facilities with adequate laboratory infrastructure. The main limitation of these tests, however, is the fact that they rely on the availability of a good quality sputum sample. They are therefore not suitable for individuals with difficulty in providing good quality sputum specimens and those with paucibacillary disease such as children and HIV infected individuals, and more particularly, patients with extra-pulmonary TB.

Tuberculosis meningitis (TBM) is the most severe form of extra pulmonary TB as it affects the central nervous system. It mostly occurs during early childhood and has high morbidity and mortality, despite the availability of adequate anti-TB therapy. This is mainly due to delayed diagnosis. Diagnosing pulmonary TB disease in children is challenging. It is even more challenging to diagnose extrapulmonary TB such as TBM (with fewer specific symptoms and signs) in children. For example, the sensitivity of the GeneXpert tests is only 50-60% for TBM and only improves to about 72% when cerebrospinal fluid (CSF) is centrifuged. As a consequence, TBM frequently results in a poor outcome.

Tests that are suitable for the diagnosis of TBM disease in all patient groups, especially children, are thus urgently needed.

SUMMARY OF THE INVENTION

According to a first embodiment of the invention, there is provided a method of diagnosing tuberculous meningitis (TBM), the method comprising the step of testing a cerebrospinal fluid (CSF) sample from a subject suspected of having TBM for the presence of MPO and at least two other biomarkers, wherein at least one of the other biomarkers is selected from the group consisting of IFN-γ, sICAM-1, VEGF-A and CXCL8.

One of the other biomarkers may be IFN-γ.

The second other biomarker may be selected from sICAM-1, VEGF-A and CXCL8.

The method may comprise testing the CSF sample for MPO, IFN-γ and at least one other biomarker selected from sICAM-1, VEGF-A and CXCL8.

For example, the method may comprise testing the CSF sample for MPO, IFN-γ and VEGF-A.

Alternatively, the method may comprise testing the CSF sample for MPO, IFN-γ, sICAM-1 and CXCL8.

The method may also comprise testing the CSF sample for one or more additional biomarkers selected from the group consisting of CCL18 (MIP-4), MIG (CXCL9), I-309 (CCL1), CCL5 (RANTES), IL-6, tumour necrosis factor (TNF)-α, matrix metalloproteinase (MMP)-9, MMP-8, complement C2 (CC2), total plasminogen activator inhibitor 1 (PAI-1), IL-1β, IP-10 (CXCL10), alpha-2-antitrypsin (A1AT), IL-10, granulocyte-macrophage colony stimulating factor (GM-CSF), CC4, CC4b, granulocyte colony stimulating factor (G-CSF), apolipoprotein (Apo)-A1, CC5a, platelet-derived growth factor (PDGF)-AB/BB, mannose-binding lectin (MBL), ferritin, CC5, serum amyloid P (SAP), complement factor H (CFH), P-Selectin, PDGF-AA, TGF-α, lipocalin-2 (NGAL), CC3, MIP-1β(CCL4), IL-17A, c-reactive protein (CRP), natural cell adhesion molecule (NCAM/CD56), CC9, CD40 ligand, complement factor 1 (CF1), MIP-1α (CCL3), D-dimer, Apo CIII, VCAM-1, IL-12/23p40, adipsin (Complement factor D), GDF-15, PEDF, MMP-1, serum amyloid A (SAA), amyloid beta-40 (Aβ40), ADMTS13, Aβ42, myoglobin, MCP-1 (CCL2), S100B, MMP-7, IL-4, sRAGE and cathepsin D.

The subject may be a child.

A capture agent may be used to bind each of the biomarkers.

One or more indicators may be provided to indicate when binding of each of the capture agents and biomarkers occurs.

Detection of one or more of the biomarkers in the sample or a measured signal which equates to a level of biomarker in the sample which is higher than a threshold level of the same biomarker may be an indicator of TBM.

According to a second embodiment of the invention, there is provided a device for diagnosing tuberculous meningitis (TBM), the device comprising:
    a means for receiving a cerebrospinal fluid (CSF) sample from a subject suspected of having TBM;
    capture agents for binding MPO and at least two other biomarkers, wherein at least one of the other biomarkers is selected from the group consisting of IFN-γ, sICAM-1, VEGF-A and CXCL8; and
    at least one indicator which indicates when the capture agents bind to the biomarkers.

The device may comprise capture agents for binding at least MPO and IFN-γ.

The device may comprise capture agents for binding MPO, IFN-γ and VEGF-A.

The device may comprise capture agents for binding MPO, IFN-γ, sICAM-1 and CXCL8.

The capture agents may be selected from the group consisting of antibodies, affybodies, ankyrin repeat proteins, armadillo repeat proteins, nucleic acid aptamers, peptides, carbohydrate ligands, synthetic ligands and synthetic polymers. Preferably, the capture agents are antibodies.

The indicator may indicate binding of the capture agent to the biomarker by electrical, electronic, acoustic, optical or mechanical methods.

The device may further include measuring means for measuring the levels of the detected biomarkers.

The device may further include amplifying means for increasing the sensitivity of the detection of the biomarkers.

The device may be a hand-held point-of-care device.

According to a third embodiment of the invention, there is provided a kit for diagnosing tuberculous meningitis (TBM), the kit comprising one or more of the following:
  capture agents for binding MPO and at least two other biomarkers, wherein at least one of the other biomarkers is selected from the group consisting of IFN-γ, sICAM-1, VEGF-A and CXCL8;
  means for obtaining or receiving a CSF sample from a subject;
  a device for diagnosing TBM; and/or
  instructions, in electronic or paper form, for performing the method as described above.

According to a further embodiment of the invention, there is provided a method of diagnosing and treating a subject with tuberculous meningitis (TBM), the method comprising the steps of:
  testing a cerebrospinal fluid (CSF) sample from a subject suspected of having TBM for the presence of MPO and at least two other biomarkers, wherein at least one of the other biomarkers is selected from the group consisting of IFN-γ, sICAM-1, VEGF-A and CXCL8;
  determining whether the subject has TBM based on the detection of the biomarkers in the sample; and
  administering an effective amount of TBM treatment to the subject if the subject is in need thereof.

According to a further embodiment of the invention, there is provided a computer implemented method for diagnosing tuberculous meningitis (TBM) in a subject, the computer performing steps comprising:
  receiving inputted subject data comprising values for levels of MPO and at least two other biomarkers in a CSF sample from the subject, wherein at least one of the other biomarkers is selected from the group consisting of IFN-γ, sICAM-1, VEGF-A and CXCL8;
  comparing these values with predetermined values for the biomarkers;
  determining whether the subject has TBM; and
  displaying information regarding the diagnosis of the subject.

According to a further embodiment of the invention, there is provided a method for diagnosing tuberculous meningitis (TBM), the method comprising the step of testing a blood sample from a subject suspected of having TBM for the presence of at least one biomarker selected from the group consisting of adipsin (complement factor D), Ab42 and IL-10, and at least two other biomarkers.

The at least one biomarker may be adipsin (complement factor D).

The at least one biomarker may be Ab42.

The at least one biomarker may be IL-10.

The method may comprise measuring the levels of adipsin (complement factor D), Ab42 and IL-10.

The method may also comprise testing the blood sample for one or more additional biomarkers selected from the group consisting of VCAM-1, MCP-1 (CCL2), IL-4, TNF-α, MIP-1β (CCL4), SAP, CC5, CFH, G-CSF, IL-10, apo CIII, IL-17A, PAI-1 (total), PDGF-AB/BB, MBL, NCAM-1, CC4b, MMP-1, CXCL8 (IL-8), CC4, sRAGE, TGF-α, IL-7, IL-6, GM-CSF, apo AI, VEGF, Aβ40, CF1, MMP-7, myoglobin, CXCL10 (IP-10), PDGF-AA, MIP4, A1AT, P-Selectin, CC5a, IL-1β, MMP-8, CRP, CCL3/MIP-1β, MMP-9, IL-21, cathepsin D, ICAM-1, CC9, MPO, CD40L, GDF-15, D-dimer, BDNF, CXCL9 (MIG), SAA, CCL1 (I-309), and IFN-γ.

The sample may be a whole blood, serum or plasma sample.

The subject may be a child.

A capture agent may be used to bind each of the biomarkers.

One or more indicators may be provided to indicate when binding of each of the capture agents and biomarkers occurs.

Detection of at least one of the biomarkers or a measured signal which equates to a level of biomarker in the sample which is higher than a threshold level of the same biomarker may be an indicator of TBM.

According to a further embodiment of the invention, there is provided a device for diagnosing tuberculous meningitis (TBM), the device comprising:
  a means for receiving a blood sample from a subject suspected of having TBM;
  capture agents for binding at least one biomarker selected from the group consisting of adipsin (complement factor D), Ab42 and IL-10, and at least two other biomarkers; and
  at least one indicator which indicates when the capture agents bind to the biomarkers.

The at least one biomarker may be adipsin (complement factor D).

The at least one biomarker may be Ab42.

The at least one biomarker may be IL-10.

The device may comprise capture agents for binding adipsin (complement factor D), Ab42 and/or IL-10.

The capture agents may be selected from the group consisting of antibodies, affybodies, ankyrin repeat proteins, armadillo repeat proteins, nucleic acid aptamers, peptides, carbohydrate ligands, synthetic ligands and synthetic polymers. Preferably, the capture agents are antibodies.

The indicator may indicate binding of the capture agent to the biomarker by electrical, electronic, acoustic, optical or mechanical methods.

The device may further include measuring means for measuring the levels of the detected biomarkers.

The device may further include amplifying means for increasing the sensitivity of the detection of the biomarkers.

The device may be a hand-held point-of-care device.

According to a further embodiment of the invention, there is provided a kit for diagnosing tuberculous meningitis (TBM), the kit comprising one or more of the following:
  capture agents for binding at least one biomarker selected from the group consisting of adipsin (complement factor D), Ab42 and IL-10, and at least two other biomarkers;
  means for obtaining or receiving a blood sample from a subject;
  a device for diagnosing TBM; and/or
  instructions, in electronic or paper form, for performing the method as described above.

According to a further embodiment of the invention, there is provided a method of diagnosing and treating a subject with tuberculous meningitis (TBM), the method comprising the steps of:
testing a blood sample from a subject suspected of having TBM for the presence of at least one biomarker selected from the group consisting of adipsin (complement factor D), Aβ42 and IL-10, and at least two other biomarkers;
determining whether the subject has TBM based on the detection of the biomarkers in the sample; and
administering an effective amount of TBM treatment to the subject if the subject is in need thereof.

According to a further embodiment of the invention, there is provided a computer implemented method for diagnosing TBM in a subject, the computer performing steps comprising:
receiving inputted subject data comprising values for levels of at least one biomarker selected from the group consisting of adipsin (complement factor D), Aβ42 and IL-10, and at least two other biomarkers in a blood sample from the subject;
comparing these values with predetermined values for the biomarkers;
determining whether the subject has TBM; and
displaying information regarding the diagnosis of the subject.

DETAILED DESCRIPTION OF THE INVENTION

Figure 1A:
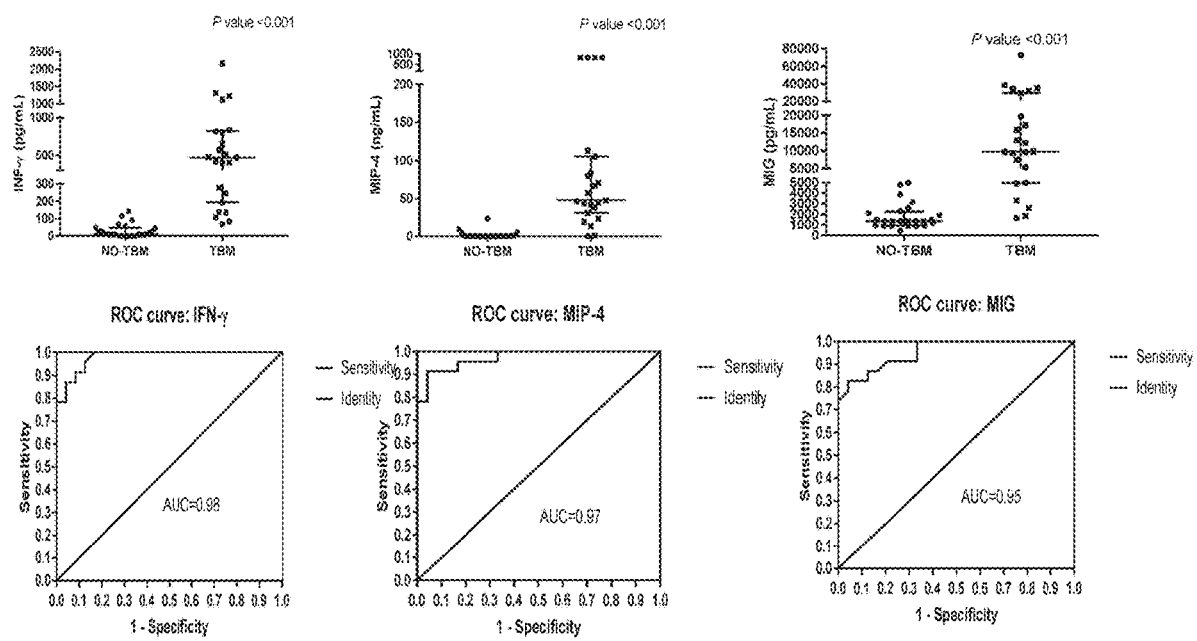
FIG. 1A: Representative plots showing the levels of biomarkers detected in cerebrospinal fluid (CSF) samples from children with TB meningitis (TBM) vs those without TBM and receiver operator characteristics (ROC) curves showing the accuracies of these biomarkers in the diagnosis of TBM. Error bars in the scatter-dot plots indicate the median and inter-quartile ranges. Representative plots for six analytes with AUC≥0.80 are shown.

A method, device, kit and computer-implemented method for diagnosing (and optionally also treating) tuberculous meningitis (TBM) are described herein.

In one embodiment, the method comprises testing a cerebrospinal fluid (CSF) sample from a subject suspected of having TBM for the presence of MPO and at least two other biomarkers, at least one of the other biomarkers being selected from the group consisting of IFN-γ, sICAM-1, VEGF-A and CXCL8.

The one other biomarker can be IFN-γ. The second other biomarker can also be selected from the remaining biomarkers in the group above, i.e. sICAM-1, VEGF-A and CXCL8. For example, the method can comprise testing the sample for MPO, IFN-γ and VEGF-A or for MPO, IFN-γ, sICAM-1 and CXCL8.

It will, of course, be possible to test the sample for additional biomarkers, such as any one or more of CCL18 (MIP-4), MIG (CXCL9), I-309 (CCL1), CCL5 (RANTES), IL-6, tumour necrosis factor (TNF)-α, matrix metalloproteinase (MMP)-9, MMP-8, complement C2 (CC2), total plasminogen activator inhibitor 1 (PAI-1), IL-1β, IP-10 (CXCL10), alpha-2-antitrypsin(A1AT), IL-10, granulocyte-macrophage colony stimulating factor (GM-CSF), CC4, CC4b, granulocyte colony stimulating factor (G-CSF), apolipoprotein (Apo)-A1, CC5a, platelet-derived growth factor (PDGF)-AB/BB, mannose-binding lectin (MBL), ferritin, CC5, serum amyloid P (SAP), complement factor H (CFH), P-Selectin, PDGF-AA, TGF-α, lipocalin-2 (NGAL), CC3, MIP-1β(CCL4), IL-17A, c-reactive protein (CRP), natural cell adhesion molecule (NCAM/CD56), CC9, CD40 ligand, complement factor 1 (CF1), MIP-1a (CCL3), D-dimer, Apo CIII, VCAM-1, IL-12/23p40, adipsin (Complement factor D), GDF-15, PEDF, MMP-1, serum amyloid A (SAA), amyloid beta-40 (Aβ40), ADMTS13, Aβ42, myoglobin, MCP-1 (CCL2), S100B, MMP-7, IL-4, sRAGE and cathepsin D.

A positive diagnosis for TBM can be made when one, two, three or more of the tested biomarkers are detected, or when the levels of the detected biomarkers are higher than a typical level of the same biomarker in subjects without TBM.

The CSF sample can be centrifuged before it is tested. Alternatively, the sample can be tested without centrifugation.

In an alternative embodiment, the method comprises testing a blood sample from a subject suspected of having TBM for the presence of at least one biomarker selected from the group consisting of adipsin (complement factor D), Ab42 and IL-10, and at least two other biomarkers, and determining whether the subject has TBM. The blood sample can be whole blood or alternatively can be serum or plasma.

It is possible to measure the levels of more than one of the above biomarkers, such as measuring the levels of at least two biomarkers (e.g. adipsin (complement factor D) and Ab42; adipsin (complement factor D) and IL-10; or Ab42 and IL-10), or measuring the levels of all three biomarkers (adipsin (complement factor D), Ab42 and IL-10). A preferred biomarker signature comprises at least adipsin (complement factor D), Ab42 and IL-10.

A positive diagnosis for TBM will be made when one, two, three or more of the tested biomarkers are detected, or when the levels of the detected biomarkers are higher than a typical level of the same biomarker in subjects without TBM.

Cut-off or threshold values can be determined based on levels of biomarkers which are typically found in patients without TBM, and the levels of the biomarkers detected in the sample can be compared to the cut-off levels when making the determination of whether or not the subject has TBM. In other words, the method will detect whether the biomarkers in the panels are under- or over-expressed relative to a subject who does not have TBM.

The methods described above can be used to diagnose TBM in all human subjects, including adults and children (e.g. children 13 years and younger).

TBM treatment can be administered to subjects who are identified as having TBM.

The method can also be used as an initial diagnostic tool whereby a positive diagnosis from this method can, if necessary, be subsequently confirmed by means of a second diagnostic method. In the interim, while waiting for the results of the second test, the subject can be started on treatment. Conversely, the method of the invention can also be used to rule out TBM, thus preventing overtreatment of non-TBM subjects.

The biomarkers can be detected using commercially available techniques, such as ELISA techniques or multiplex bead array technology, although it is intended that a specific point-of-care (or bedside) diagnostic device will be used for performing the method, particularly for use in resource poor settings. Such a device will lead to a significant reduction in the costs and delays that are currently incurred in the diagnosis of TBM, with a consequent reduction in morbidity and mortality.

In one embodiment, the device has a means for receiving the sample from the subject, such as a loading or receiving area onto or into which the sample is placed. Capture agents and indicators are present in the device, and once the sample has been loaded onto or received into the device, the sample is brought into contact with the capture agents, which are allowed to bind to the biomarkers if present. The indicator will signify that binding has occurred. The device may further include amplifying means for increasing the sensitivity of the detection of the biomarkers.

The capture agents can be antibodies, affybodies, ankyrin repeat proteins, armadillo repeat proteins, nucleic acid aptamers, peptides, carbohydrate ligands, synthetic ligands or synthetic polymers. Typically, however, the capture agents are antibodies. The indicator can be a calorimetric, electrical, electrochemical, electronic, chromogenic, optical, fluorescent or a radio-labeled indicator.

For example, the point-of-care device can be a lateral flow device similar to those known in the art. This can be dipped into the cerebrospinal fluid or blood sample, or the sample can be placed onto a portion of the device commonly known as the sample pad. Fluid from the sample migrates to a portion of the device containing the capture agents, which generate a signal when they bind to the biomarkers in the panel. The device may use up-converting phosphor technology.

Another example of a suitable point-of-care assay makes use of biosensors comprising a transducer element, for the conversion of the biological signal to an electronic signal, to which antibodies against the biomarkers can be immobilised. The transducer element can use different conversion mechanisms, such as piezoelectricity or impedance changes, and can be implemented on different substrates, such as electrospun nanofiber meshes or paper. Depending on the chosen transducer element, the binding of the target molecules in the samples to the immobilised capture antibodies results in the generation of piezoelectric energy or a change in impedance, proportional to the amount of target molecule detected in the sample. The measured data are stored in the handheld device containing the biosensing elements, but can also be downloaded to a database or cloud for further analysis.

A kit can also be provided to enable the method of the invention to be performed. The kit could include one or more of the following:
  capture agents, such as antibodies, for binding the intended biomarkers;
  a means for obtaining or receiving a CSF or blood sample from a subject;
  a point-of-care device as described above; and/or
  instructions, in electronic or paper form, for performing the method.

The invention further provides a computer implemented method for diagnosing TBM in a subject, the computer performing steps comprising:
  a) receiving inputted subject data comprising values for levels of the biomarkers of interest in a CSF or blood sample from the subject;
  b) comparing these values with predetermined values for the biomarkers;
  c) determining whether the subject has TBM; and
  d) displaying information regarding the diagnosis of the subject.

The subject may be diagnosed with TBM if one or more of the biomarkers is detected in the sample, or if the measured levels of the biomarkers in the sample are higher than a predetermined value for the biomarkers. The predetermined value is generally based on typical levels of the same biomarker in subjects without TBM.

The invention will now be described in more detail by way of the following non-limiting examples.

EXAMPLES

Materials and Methods

Participants for the present study were recruited from Tygerberg Academic Hospital in the Western Cape Province of South Africa. All children between the ages of 3 months and 13 years with suspected meningitis, and who required CSF examination for routine diagnostic purposes at Tygerberg Children's Hospital, were eligible for inclusion in the study, provided the written informed consent was obtained from the parents or legal guardians. Assent was obtained from children older than 7 years who had a normal level of consciousness, i.e. a Glasgow Coma Score (GCS) of 15/15. Children older than 13 years and those who refused to provide written consent or assent were excluded from the study. The study was approved by the Health Research Ethics Committee of the University of Stellenbosch, Tygerberg Hospital and the Western Cape Provincial Government.

Sample Collection and Processing

After the collection of samples for processing for routine diagnostic purposes, an additional 1 ml of CSF was collected into a sterile tube, followed by the collection of 1 ml of whole blood into a serum blood tube. Samples were then sent to the Stellenbosch University Immunology Research laboratory, for further processing for research purposes, within an average period of 2 hours from collection. Serum samples were centrifuged at 1200 g for 10 minutes, followed by aliquoting and storage at −80° C. until processed further as described below. CSF samples were centrifuged in a biosafety level 3 laboratory at 4000 g for 15 minutes, after which they were aliquoted and stored at −80° C. until analysed with the Luminex platform as described below.

Diagnostic Work-Up of Study Participants

All patients underwent a comprehensive clinical evaluation by a specialist paediatric neurologist. After routine special investigations, computed temography (CT) of the brain, air-encephalography, and magnetic resonance (MR) imaging were done as clinically indicated. Following lumbar puncture, investigations including appearance and colour determination, differential cell counts, protein, glucose and other markers were assessed, followed by centrifugation of the CSF, Gram staining, India ink examination, culture of the centrifuged sediment on blood agar plates (for pyogenic bacteria), Auramine "O" staining and fluorescence microscopy, culture using the BBLTMMGIT (*Mycobacterium* Growth Indicator Tubes)™ (Becton and Dickinson) and examination for MTB DNA using the HAIN Genotype MTBDRplus kit. All data were recorded in a Red Cap we-based database.

A diagnosis of probable TBM was made if two or more of the following criteria were present in the setting of a characteristic history and CSF changes associated with TBM: a positive history of contact with an adult TB case, a positive tuberculin skin test, a chest x-ray suggestive of pulmonary tuberculosis (hilar lymphadenopathy, miliary tuberculosis or cavitation), CT or MRI demonstrating the characteristic features of TBM (ventricular dilatation, meningovascular enhancement and/or granuloma/s), poor weight gain or weight crossing percentiles documented on health cards or positive identification of acid fast bacilli from gastric washings (microscopy or culture). A diagnosis of definite TBM was made if acid-fast bacilli were present in the CSF, MTB was cultured from CSF, a nucleic acid amplification test of CSF yielded positive results or if there was histopathological evidence of MTB from another central nervous system site.

Luminex Multiplex Immunoassay

The concentrations of 69 candidate biomarkers were evaluated using the Luminex platform. Some of these have not previously been investigated in TB, while others have previously shown potential as possible diagnostic biomarkers in serum and plasma samples from adult pulmonary TB suspects for TBM disease. These included CCL1/I-309, CCL2/MCP-1, CCL3/MIP-1α, CCL4/MIP-1β, CD40 ligand (CD40L), CXCL10/IP-10, CXCL8/IL-8, CXCL9/MIG, G-CSF, GM-CSF, IFN-γ, IL-1β, IL-10, IL-12/23 (p40), IL-17A, IL-21, IL-4, IL-6, IL-7, MMP-1, MMP-8, TGF-α, TNF-α, sNCAM-1/CD56, MMP-7, ferritin, MMP-9 (R&D Systems), apolipoprotein (Apo)-AI, Apo-CIII, complement C3, complement factor H, BDNF, cathepsin D, sICAM-1, myeloperoxidase (MPO), PDGF_AA, RANTES, PDGF_AB_BB, sVCAM1, PAI-1 (total), S100B, A-Beta-1-40 (Ab40), A-Beta-1-42 (Ab42), sRAGE, GDNF, CRP, alpha-2-antitrypsin (A1AT), PEDF, SAP, MIP-4/PARC/CCL18, complement C4 (CC4), CC2, CC4b, CC5, CC5a, CC9, adipson/complement factor D (ADPSN), mannose binding lectin (MBL), complement factor 1 (CF1), sP-selectin, ADAMTS13, D-DIMER, GDF-15, myoglobin, lipocalin2/NGAL, SAA (Merck Millipore), IL-13, VEGF A and cathelicidin LL-37. All these biomarkers were evaluated on CSF and serum samples collected from the TBM study participants, following the instructions of the respective kit manufacturers. All experiments were performed on the Bio Plex Luminex platform (Bio Rad Laboratories, Hercules, USA) and data acquisition and analysis of median fluorescent intensities was done using the Bio Plex Manager version 6.1 software (Bio Rad Laboratories). The laboratory staff performing the Luminex experiments were blinded to the clinical classifications of the study participants.

Statistical Analysis

Differences in the concentrations of host biomarkers between the TBM and the no-TBM group were assessed using the Mann Whitney U test. The Receiver Operator Characteristics (ROC) curve analysis procedure was used to ascertain the diagnostic accuracy of individual host biomarkers in diagnosing TBM. The utility of combinations of biomarkers in the diagnosis TBM disease was ascertained by the General Discriminant Analysis (GDA), followed by leave-one-out cross validation. This method was chosen because of the relatively limited sample size. The data was analysed using Statistica (Dell, USA), and GraphPad Prism version 5.

Results

A total of 47 children with suspected TBM were included in the study, of whom 23 were diagnosed with TBM and 24 without, with other causes of meningitis (no-TBM group). The no-TBM group included children with bacterial meningitis and viral meningitis, amongst others. The characteristics of the study participants are shown in Table 1.

TABLE 1

Clinical and demographic characteristics of children included in the study.

|  | All | TBM | no-TBM |
| --- | --- | --- | --- |
| Number of participants | 47 | 23 | 24 |
| Mean age (Months) ± SD | 41.6 ± 41.5 | 31.5 ± 34.8 | 51.3 ± 45.7 |
| Females/Males ratio | 17/30 | 10/13 | 7/17 |
| HIV Positive (n/number done) | 6/37 | 0/22 | 6/15 |

Figure 1:
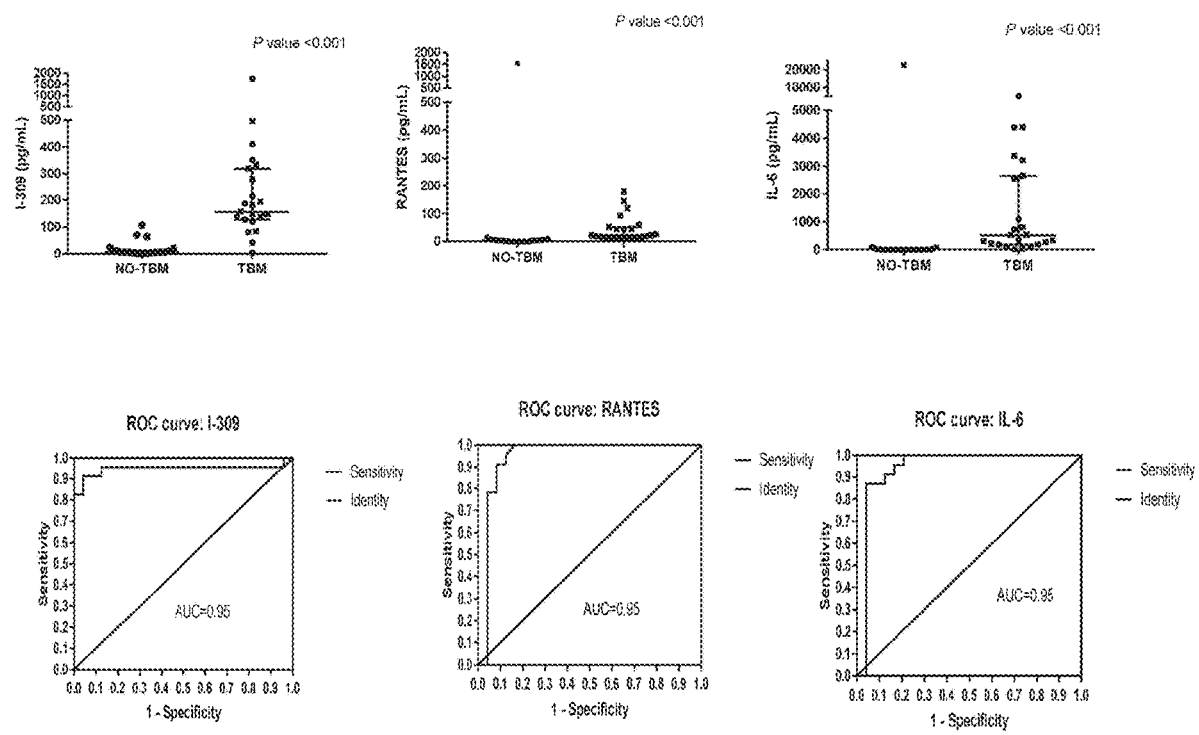
FIG. 1B: Representative plots showing the levels of biomarkers detected in cerebrospinal fluid (CSF) samples from children with TB meningitis (TBM) vs those without TBM and receiver operator characteristics (ROC) curves showing the accuracies of these biomarkers in the diagnosis of TBM. Error bars in the scatter-dot plots indicate the median and inter-quartile ranges. Representative plots for six analytes with AUC≥0.80 are shown.

Utility of Individual Host Biomarkers Detected in CSF Samples from Children in the Diagnosis of TBM As shown in Table 2, the expression of multiple host markers was significantly different in CSF samples obtained from children with TBM in comparison to those without TBM. When the data for individual CSF host biomarkers were analysed using the receiver operator characteristics (ROC) curve procedure, the area under the ROC curve (AUC) was above 0.70 for 47 of the 70 candidate biomarkers investigated (Table 2). Of note, the AUCs for 29 of these host markers, including IFN-γ, MIP-4, CXCL9, CCL1, RANTES, IL-6, TNF-α, MPO, MMP-9, MMP-8, CC2, IL-10, PAI-1, CXCL8, IL-1b, A1AT, CXCL10, G-CSF, CC4, CC4b, GM-CSF, PDGF AB/BB, Apo-AI, MBL, ferritin, CC5a, SAP, CC5 and VEGF A were 0.80, with individual host biomarkers detectable in the CSF diagnosing TBM with promising sensitivities and specificities (Table 2, FIG. 1).

TABLE 2

Utility of individual host markers detectable in CSF samples from children in the diagnosis of TB meningitis. Median levels (inter-quartile ranges in parenthesis) of all host markers detected in CSF samples from children with TBM or no-TBM and the accuracies in the diagnosis of TBM disease as determined by ROC curve analysis are shown. Cut-off values and associated sensitivities and specificities were selected based on the Youden's index.

| Host marker | Median in TBM (IQR) | Median in No-TBM (IQR) | p-value | AUC (95% CI) | Cut-off Value | Sensitivity % (95% CI) | Specificity % (95% CI) |
|---|---|---|---|---|---|---|---|
| IFN-γ | 469.9 (194.0-818.1) | 10.3 (3.9-45.7) | <0.0001 | 0.98 (0.95-1.00) | >99.5 | 91.3 (72.0-98.9) | 91.7 (73.0-99.0) |
| MIP-4 | 47.5 (31.0-105.4) | 0.3 (0.2-0.8) | 0 < 0.0001 | 0.97 (0.94-1.00) | >11.4 | 91.3 (72.0-98.9) | 95.8 (78.9-99.9) |
| MIG/CXCL9 | 9846.2 (4983.6-29684.1) | 1349.7 (929.7-2205.9) | <0.0001 | 0.95 (0.90-1.00) | >4855.0 | 82.6 (61.2-95.0) | 95.8 (78.9-99.9) |
| I-309/CCL1 | 156.6 (127.2-318.9) | 5.4 (3.8-11.4) | <0.0001 | 0.95 (0.87-1.00) | >74.6 | 91.3 (72.0-98.9) | 95.8 (78.9-99.9) |
| RANTES | 22.3 (14.6-52.0) | 3.8 (0.1-5.7) | <0.0001 | 0.95 (0.87-1.00) | >9.9 | 91.3 (72.0-98.9) | 91.7 (73.0-99.0) |
| IL-6 | 524.8 (196.3-2659.9) | 2.8 (1.1-12.3) | <0.0001 | 0.95 (0.88-1.00) | >100.7 | 87.0 (66.4-97.2) | 95.8 (78.9-99.9) |
| TNF-α | 69.2 (50.9-137.6) | 1.2 (0.0-8.5) | <0.0001 | 0.93 (0.85-1.00) | >19.8 | 95.7 (78.1-99.9) | 87.5 (67.6-97.3) |
| MPO | 62078.8 (49640.6-73505.9) | 1430.5 (495.4-5436.1) | <0.0001 | 0.93 (0.83-1.02) | >25823.0 | 95.7 (78.1-99.9) | 91.7 (73.0-99.0) |
| MMP-9 | 4074.6 (2081.8-7163.1) | 8.6 (0.0-198.8) | <0.0001 | 0.91 (0.81-1.00) | >963.9 | 95.7 (78.1-99.9) | 91.7 (73.0-99.0) |
| MMP-8 | 8640.1 (2811.4-23467.6) | 257.3 (0.0-1075.2) | 0.000002 | 0.91 (0.82-1.00) | >1695 | 91.3 (72.0-98.9) | 83.3 (62.6-95.3) |
| CC2 | 2188.4 (1229.9-180000.0) | 87.5 (41.8-558.7) | 0.000006 | 0.89 (0.78-0.99) | >712 | 87.0 (66.4-97.2) | 83.3 (62.6-95.3) |
| PAI-1 | 6090.8 (2456.8-12786.0) | 401.6 (194.4-1189.3) | 0.000008 | 0.88 (0.77-0.99) | >2163 | 82.6 (61.2-95.1) | 87.5 (67.6-97.3) |
| IL-1β | 47.9 (24.2-64.3) | 0.0 (0.0-9.7) | 0.000009 | 0.87 (0.76-0.99) | >12.9 | 82.6 (61.2-95.1) | 79.2 (57.9-92.9) |
| IL-8/CXCL8 | 970.6 (519.7-1550.8) | 110.2 (50.2-331.2) | 0.000010 | 0.88 (0.77-0.99) | >394.8 | 87.0 (66.4-97.2) | 79.2 (57.9-92.9) |
| IP-10/CXCL10 | 44900.0 (2102.7-44900.0) | 257.6 (85.5-837.4) | 0.000016 | 0.86 (0.75-0.97) | >1200 | 95.7 (78.1-97.2) | 79.2 (57.9-92.9) |
| A1AT | 2209.8 (916.0-6488.9) | 338.4 (236.8-866.1) | 0.000023 | 0.87 (0.75-0.98) | >715.3 | 91.3 (72.0-98.9) | 75.0 (53.3-90.2) |
| IL-10 | 47.8 (22.2-82.4) | 5.3 (0.0-12.0) | 0.000037 | 0.88 (0.76-1.00) | >15.3 | 91.3 (72.0-98.9) | 87.0 (67.6-97.3) |
| G-CSF | 400.2 (178.1-561.0) | 0.0 (0.0-152.9) | 0.000043 | 0.85 (0.73-0.97) | >137.5 | 91.3 (72.0-98.9) | 75.0 (53.3-90.2) |
| CC4 | 1201.2 (667.0-2196.0) | 336.2 (232.7-593.2) | 0.000060 | 0.84 (0.73-0.96) | >653.3 | 78.3 (56.3-92.5) | 79.2 (57.9-92.9) |
| CC4b | 565.7 (377.5-668.8) | 172.7 (94.3-331.7) | 0.000103 | 0.83 (0.71-0.96) | >364.7 | 78.3 (56.3-92.5) | 79.2 (57.9-92.9) |
| GM-CSF | 88.9 (64.7-105.1) | 27.9 (13.4-60.5) | 0.000112 | 0.81 (0.71-0.95) | >63.8 | 78.3 (56.3-92.5) | 79.2 (57.9-92.9) |

TABLE 2-continued

Utility of individual host markers detectable in CSF samples from children in the diagnosis of TB meningitis. Median levels (inter-quartile ranges in parenthesis) of all host markers detected in CSF samples from children with TBM or no-TBM and the accuracies in the diagnosis of TBM disease as determined by ROC curve analysis are shown. Cut-off values and associated sensitivities and specificities were selected based on the Youden's index.

| Host marker | Median in TBM (IQR) | Median in No-TBM (IQR) | p-value | AUC (95% CI) | Cut-off Value | Sensitivity % (95% CI) | Specificity % (95% CI) |
|---|---|---|---|---|---|---|---|
| Apo AI | 1708.0 (980.1-7429.6) | 150.8 (0.0-980.1) | 0.000167 | 0.82 (0.69-0.95) | >365.4 | 91.3 (72.0-98.9) | 70.8 (48.9-87.4) |
| CC5a | 66.7 (35.1-93.0) | 6.4 (4.4-42.8) | 0.000173 | 0.81 (0.68-0.95) | >26.0 | 82.6 (61.2-95.1) | 70.8 (48.9-87.4) |
| PDGF-AB/BB | 12.9 (5.8-24.5) | 5.0 (0.9-7.0) | 0.000175 | 0.82 (0.69-0.95) | >7.7 | 69.6 (47.1-86.8) | 87.5 (67.6-97.3) |
| MBL | 12.3 (3.7-56.2) | 1.0 (0.6-6.6) | 0.000221 | 0.81 (0.69-0.94) | >2.9 | 87.0 (66.4-97.2) | 66.7 (44.7-84.4) |
| Ferritin | 4697.7 (3261.4-300000.0) | 705.7 (325.5-3376.9) | 0.000236 | 0.81 (0.68-0.94) | >2729 | 91.3 (72.0-98.9) | 75.0 (53.3-90.2) |
| VEGF-A | 45.4 (15.1-150.2) | 3.1 (2.5-8.1) | 0.000300 | 0.81 (0.67-0.94) | >9.4 | 82.6 (61.2-95.1) | 79.2 (57.9-92.9) |
| CC5 | 344.7 (166.1-724.3) | 36.2 (20.8-178.0) | 0.000309 | 0.81 (0.67-0.94) | >155.4 | 82.6 (61.2-95.1) | 75.0 (53.3-90.2) |
| SAP | 63.4 (34.6-184.6) | 9.6 (5.7-33.5) | 0.000364 | 0.81 (0.67-0.95) | >30.8 | 87.0 (66.4-97.2) | 75.0 (53.3-90.2) |
| CFH | 1242.8 (669.1-5717.9) | 238.9 (82.8-795.3) | 0.000629 | 0.79 (0.66-0.93) | >850.9 | 73.9 (51.6-89.8) | 78.3 (56.3-92.5) |
| ICAM-1 | 2128.5 (1610.6-4313.7) | 499.8 (319.5-1190.1) | 0.000743 | 0.79 (0.65-0.93) | >1372 | 82.6 (61.2-95.1) | 79.2 (57.9-92.9) |
| P-Selectin | 1.2 (0.0-1.8) | 0.0 (0.0-0.0) | 0.001036 | 0.76 (0.62-0.89) | >0.3 | 73.9 (51.6-89.8) | 83.3 (62.6-95.3) |
| PDGF-AA | 13.6 (7.3-19.9) | 5.5 (3.5-7.8) | 0.001047 | 0.78 (0.64-0.92) | >6.6 | 82.6 (61.2-95.1) | 75.0 (53.3-90.2) |
| TGF-α | 10.0 (5.8-25.7) | 3.7 (0.0-7.3) | 0.001048 | 0.78 (0.65-0.92) | >8.6 | 73.9 (51.6-89.8) | 83.3 (62.6-95.3) |
| NGAL | 77.8 (16.8-512.8) | 1.7 (0.7-7.3) | 0.001401 | 0.78 (0.61-0.94) | >16.8 | 78.3 (56.3-92.5) | 95.8 (78.9-99.9) |
| CC3 | 886.7 (357.8-1722.5) | 192.8 (56.5-749.1) | 0.002344 | 0.76 (0.62-0.91) | >528.6 | 73.9 (51.6-89.8) | 69.6 (47.1-86.8) |
| MIP-1β/CCL4 | 356.3 (240.6-624.8) | 185.9 (122.5-261.6) | 0.002480 | 0.76 (0.62-0.90) | >261.6 | 69.6 (47.1-86.8) | 75.0 (53.3-90.2) |
| IL-17A | 14.9 (4.9-32.5) | 0.0 (0.0-9.2) | 0.002642 | 0.75 (0.60-0.89) | >2.6 | 82.6 (61.2-95.1) | 66.7 (44.7-84.4) |
| CRP | 230000.0 (522.0-230000.0) | 361.6 (64.1-230000.0) | 0.003122 | 0.74 (0.60-0.87) | >116193.43 | 69.6 (47.1-86.8) | 70.8 (48.9-87.4) |
| NCAM | 30138.4 (18759.6-35617.2) | 41021.7 (31229.8-52874.4) | 0.003673 | 0.75 (0.61-0.89) | <36722 | 78.3 (56.3-92.5) | 66.7 (44.7-84.4) |
| CC9 | 43.1 (35.5-59.0) | 27.3 (20.7-35.8) | 0.004645 | 0.74 (0.59-0.90) | >36.6 | 73.9 (51.6-89.8) | 83.3 (62.6-95.3) |
| CD40L | 471.7 (350.8-823.8) | 263.7 (160.1-426.2) | 0.006422 | 0.73 (0.58-0.88) | >369.6 | 73.9 (51.6-89.8) | 75.0 (53.3-90.2) |
| CF1 | 480.3 (246.4-970.6) | 111.3 (83.2-369.5) | 0.006448 | 0.73 (0.58-0.88) | >263.4 | 73.9 (51.6-89.8) | 70.8 (48.9-87.4) |
| MIP-1α/CCL3 | 277.3 (208.8-348.8) | 179.0 (35.1-262.5) | 0.007518 | 0.73 (0.58-0.87) | >223.9 | 69.6 (47.1-86.8) | 70.8 (48.9-87.4) |

TABLE 2-continued

Utility of individual host markers detectable in CSF samples from children in the diagnosis of TB meningitis. Median levels (inter-quartile ranges in parenthesis) of all host markers detected in CSF samples from children with TBM or no-TBM and the accuracies in the diagnosis of TBM disease as determined by ROC curve analysis are shown. Cut-off values and associated sensititivies and specificities were selected based on the Youden's index.

| Host marker | Median in TBM (IQR) | Median in No-TBM (IQR) | p-value | AUC (95% CI) | Cut-off Value | Sensitivity % (95% CI) | Specificity % (95% CI) |
|---|---|---|---|---|---|---|---|
| D-dimer | 98000.0 (1425.0-98000.0) | 95.7 (2.5-1581.2) | 0.007729 | 0.72 (0.56-0.87) | >49857.38 | 73.9 (51.6-89.8) | 79.2 (57.9-92.9) |
| Apo CIII | 69.8 (22.7-442.0) | 14.2 (6.5-48.4) | 0.015650 | 0.71 (0.56-0.87) | >26.3 | 73.9 (51.6-89.8) | 69.6 (47.1-86.8) |
| IL-12/23p40 | 249.0 (0.00-695.8) | 0.0 (0.0-181.8) | 0.018510 | 0.69 (0.54-0.84) | >168.7 | 69.6 (47.1-86.8) | 75.0(53.3-90.2) |
| VCAM-1 | 119507.9 (45091.2-149043.0) | 41549.9 (17719.0-122798.7) | 0.020942 | 0.70 (0.55-0.85) | >79387.1 | 69.6 (47.1-86.8) | 66.7 (44.7-84.4) |
| Adipsin/Complement factor D | 50.1 (37.6-168.9) | 26.1 (15.8-64.7) | 0.046258 | 0.67 (0.51-0.83) | >35.5 | 82.6 (61.2-95.1) | 62.5(40.6-81.2) |
| GDF-15 | 0.4 (0.2-0.5) | 0.0 (0.0-0.2) | 0.049282 | 0.67 (0.50-0.84) | >0.2 | 73.9 (51.6-89.8) | 79.2 (57.9-92.9) |
| PEDF | 746.8 (667.8-837.2) | 658.0 (575.6-819.8) | 0.056793 | 0.66 (0.50-0.83) | >689.6 | 73.9 (51.6-89.9) | 62.5 (40.6-81.2) |
| MMP-1 | 448.8 (328.8-1058.9) | 308.9 (243.0-581.1) | 0.058111 | 0.66 (0.50-0.82) | >318.9 | 78.3 (56.3-92.5) | 58.3 (36.6-77.9) |
| SAA | 450.4 (1.5-230000.0) | 6.5 (0.1-254.2) | 0.059259 | 0.66 (0.50-0.82) | >204.9 | 60.9 (38.5-80.3) | 75.0 (53.3-90.2) |
| Aβ40 | 580.0 (305.1-918.5) | 800.5 (323.6-2195.3) | 0.190601 | 0.61 (0.44-0.78) | <759.5 | 65.2 (42.7-83.6) | 58.3 (36.6-77.9) |
| ADMTS13 | 8.1 (6.3-15.9) | 6.1 (0.5-9.7) | 0.212312 | 0.60 (0.44-0.77) | >6.2 | 78.3 (56.3-92.5) | 54.2 (32.8-74.5) |
| Aβ42 | 172.8 (54.3-288.2) | 219.0 (81.9-645.3) | 0.259233 | 0.60 (0.43-0.76) | <292.1 | 78.3 (56.3-92.5) | 41.7 (22.1-63.4) |
| Myoglobin | 0.5 (0.1-1.1) | 0.1 (0.0-0.9) | 0.266718 | 0.60 (0.43-0.76) | >0.2 | 73.9 (51.6-89.8) | 58.3 (36.6-77.9) |
| MCP-1/CCL2 | 812.5 (457.9-1348.7) | 1076.2 (513.2-1423.7) | 0.292145 | 0.59 (0.42-0.76) | <881.0 | 60.9 (38.5-80.3) | 66.7 (44.7-84.4) |
| S100B | 41.2 (41.2-2800.0) | 41.2 (28.0-64.6) | 0.311691 | 0.59 (0.42-0.77) | >64.6 | 38.9 (17.3-64.3) | 75.0 (50.9-91.3) |
| IL-13 | 671.68 (246.08-1409.68) | 378.2 (89.0-870.4) | 0.322220 | 0.58 (0.42-0.75) | >524.9 | 52.2 (30.6-73.2) | 66.7 (44.7-84.4) |
| MMP-7 | 101.5 (81.6-181.6) | 101.5 (81.6-121.5) | 0.329877 | 0.58 (0.42-0.75) | >111.5 | 43.5 (23.2-65.5) | 70.8 (48.9-87.4) |
| IL-4 | 162.6 (107.9-229.2) | 191.6 (132.7-248.9) | 0.394463 | 0.57 (0.40-0.74) | <181.1 | 65.2 (42.7-83.6) | 58.3 (36.6-77.9) |
| sRAGE | 14.1 (12.8-15.3) | 14.4 (12.8-16.6) | 0.473024 | 0.56 (0.39-0.73) | <14.4 | 56.5 (34.5-76.8) | 50.0 (29.1-70.9) |
| Cathepsin D | 75722.1 (61184.2-91429.2) | 66539.1 (50433.7-96857.8) | 0.537070 | 0.55 (0.38-0.72) | >68062.19 | 69.6 (47.1-86.8) | 54.2 (32.8-74.5) |
| Cathelicidin-LL37 | 0.1 (0.1-0.1) | 0.0 (0.1-0.1) | 0.619521 | 0.55 (0.38-0.71) | >0.0 | 69.6 (47.1-86.8) | 50.0 (29.1-70.9) |
| IL-7 | 4.3 (0.0-7.0) | 5.3 (2.4-7.9) | 0.645745 | 0.54 (0.37-0.71) | <4.3 | 52.2 (30.6-73.2) | 58.3 (36.6-77.9) |
| BDNF | 0.6 (0.0-1.1) | 0.5 (0.0-1.0) | 0.674752 | 0.54 (0.37-0.70) | >0.5 | 60.9 (38.5-80.3) | 50.0 (29.1-70.9) |

TABLE 2-continued

Utility of individual host markers detectable in CSF samples from children in the diagnosis of TB meningitis. Median levels (inter-quartile ranges in parenthesis) of all host markers detected in CSF samples from children with TBM or no-TBM and the accuracies in the diagnosis of TBM disease as determined by ROC curve analysis are shown. Cut-off values and associated sensititivies and specificities were selected based on the Youden's index.

| Host marker | Median in TBM (IQR) | Median in No-TBM (IQR) | p-value | AUC (95% CI) | Cut-off Value | Sensitivity % (95% CI) | Specificity % (95% CI) |
|---|---|---|---|---|---|---|---|
| IL-21 | 43.2 (12.7-78.2) | 46.8 (30.9-61.1) | 0.781809 | 0.52 (0.35-0.69) | <37.36 | 47.8 (26.8-69.4) | 66.7 (44.7-84.4) |
| GDNF | 2.2 (1.8-2.3) | 2.1 (1.9-2.5) | 0.828794 | 0.48 (0.31-0.65) | <2.1 | 47.8 (26.8-69.4) | 41.7 (22.1-63.4) |

Utility of Combinations of Host Biomarkers Detected in the CSF in the Diagnosis of TB Meningitis Based on the CSF data obtained from the study participants, the biomarkers MPO and IFN-γ were selected for incorporation into a potential CSF biosignature for TBM. General Discriminant Analysis (GDA) models of the data showed that optimal prediction of TBM using these biomarkers was achieved with combinations of 3 or 4 biomarkers.

a) Four-Marker CSF Biosignature for TBM

Figure 2:
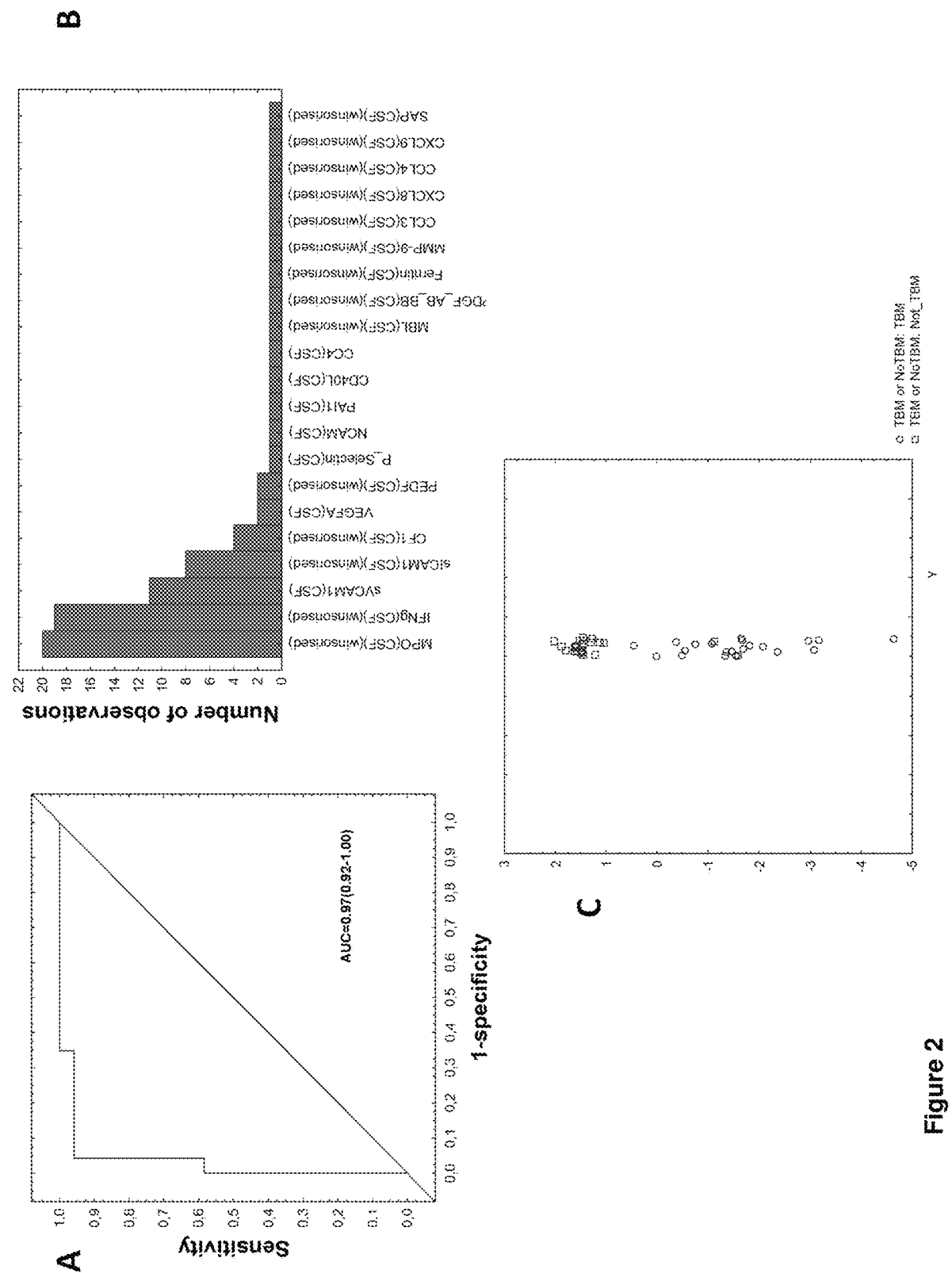
FIG. 2: Accuracy of a 4-marker CSF biosignature (sICAM-1, MPO, CXCL8 and IFN-γ) in the diagnosis of TBM. ROC curve showing the accuracy of the 4-marker biosignature (A), frequency of analytes detected in CSF in the top 20 GDA models that most accurately classified study participants as TBM or no TBM (B), and scatter plot showing the ability of the 4-marker signature in classifying children as TBM or no TBM disease. The bar graphs in B indicate the number of times each marker was included in the top 20 four-marker biosignatures, the squares in C represent the children with no TBM and the circles represent the children with TBM.

The most accurate four-marker biosignature comprising MPO, IFN-γ, sICAM-1 and CXCL8 diagnosed TBM with an AUC of 0.97 (95% confidence interval, 0.92 to 1.00), corresponding to a sensitivity of 87% (20/23) and specificity of 95.8% (23/24). After leave-one-out cross validation, there was no change in the sensitivity and specificity of the four-marker biosignature. After further optimization of the four-marker biosignature by the selection of better cut-off values, both the sensitivity and specificity of the biosignature increased to 96% (FIG. 2).

b) Three-Marker CSF Biosignature for TBM

Figure 3:
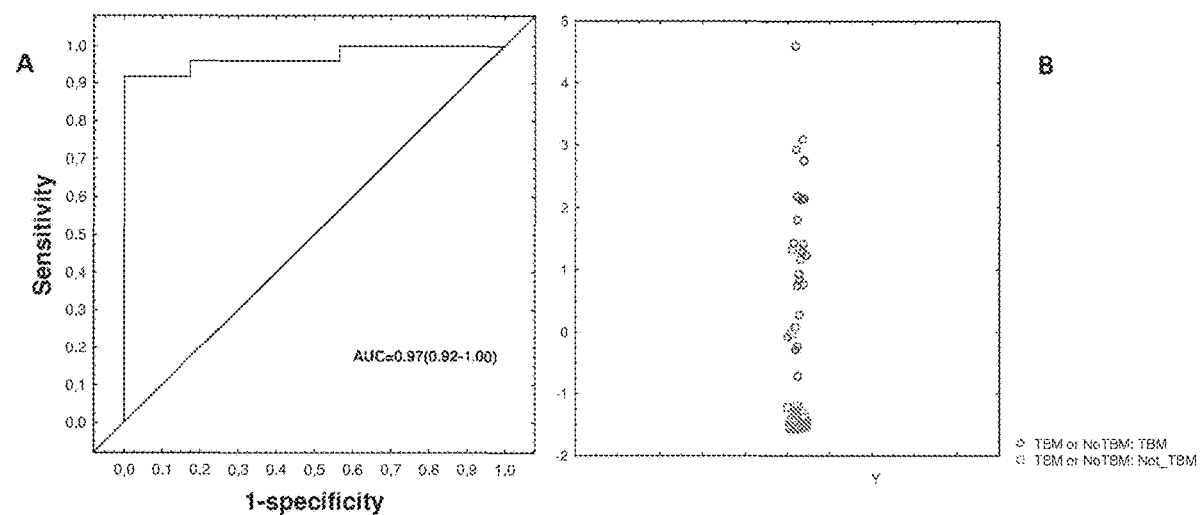
FIG. 3: Accuracy of a 3-marker CSF biosignature (VEGF, IFN-γ and MPO) in the diagnosis of TBM. ROC curve showing the accuracy of the three-marker biosignature (A), and scatter plot showing the ability of the 3-marker signature in classifying children as TBM or no TBM disease (B). The squares in B represent the children with no TBM and the circles represent the children with TBM.

A 3-marker biosignature for TBM was also identified, comprising MPO, IFN-γ and VEGF. This signature discriminated between the children with TBM and those without TBM with an AUC 0.97 (95% confidence interval, 0.92 to 1.00), corresponding to a sensitivity of 82.6% and specificity of 95.8%. After leave-one-out cross validation, the sensitivity of the biosignature was 78.3% and the specificity was 91.7%, but further optimization through the selection of better cut-off values resulted in an improved sensitivity and specificity of 92% and 100%, respectively (FIG. 3).

Utility of Host Biomarkers Detectable in Blood (Serum Samples) in the Diagnosis of TB Meningitis Whole peripheral blood was collected from all study participants from whom CSF samples were collected (all the children recruited into the study) and serum samples were obtained as described above. The host biomarkers evaluated in CSF samples were also evaluated on the serum samples. As most of the serum markers were not normally distributed, data were log transformed prior to statistical modelling applications (GDA).

Figure 4A:
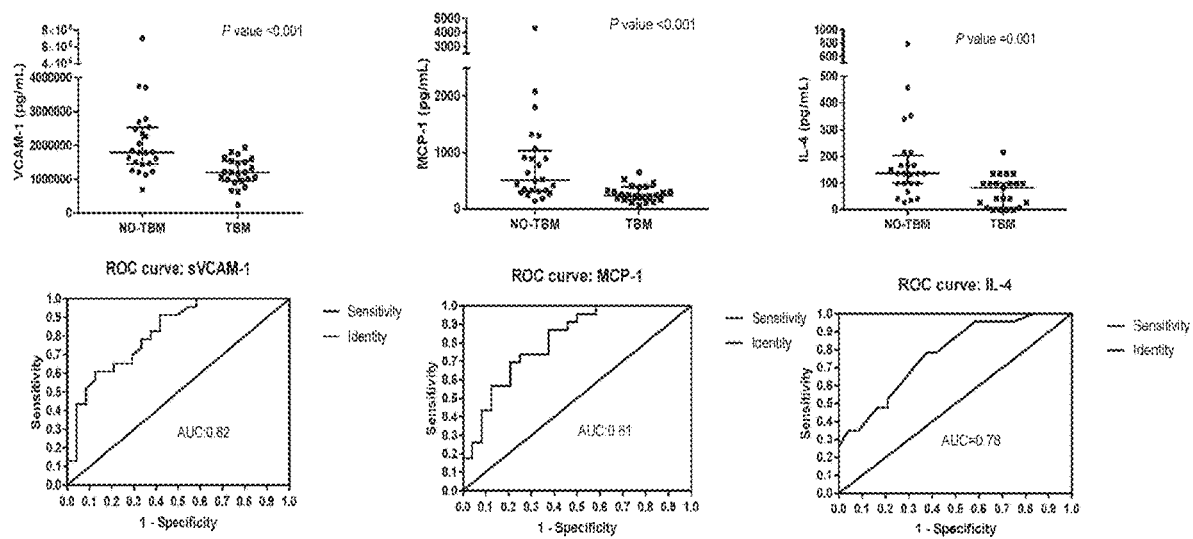
FIG. 4A: Representative plots showing the levels of biomarkers detected in serum samples from children with TBM vs those without TBM and receiver operator characteristics (ROC) curves showing the accuracies of these biomarkers in the diagnosis of TB meningitis. Error bars in the scatter-dot plots indicate the median and inter-quartile ranges. Representative plots for six analytes with AUC≥0.75 are shown.
Figure 4B:
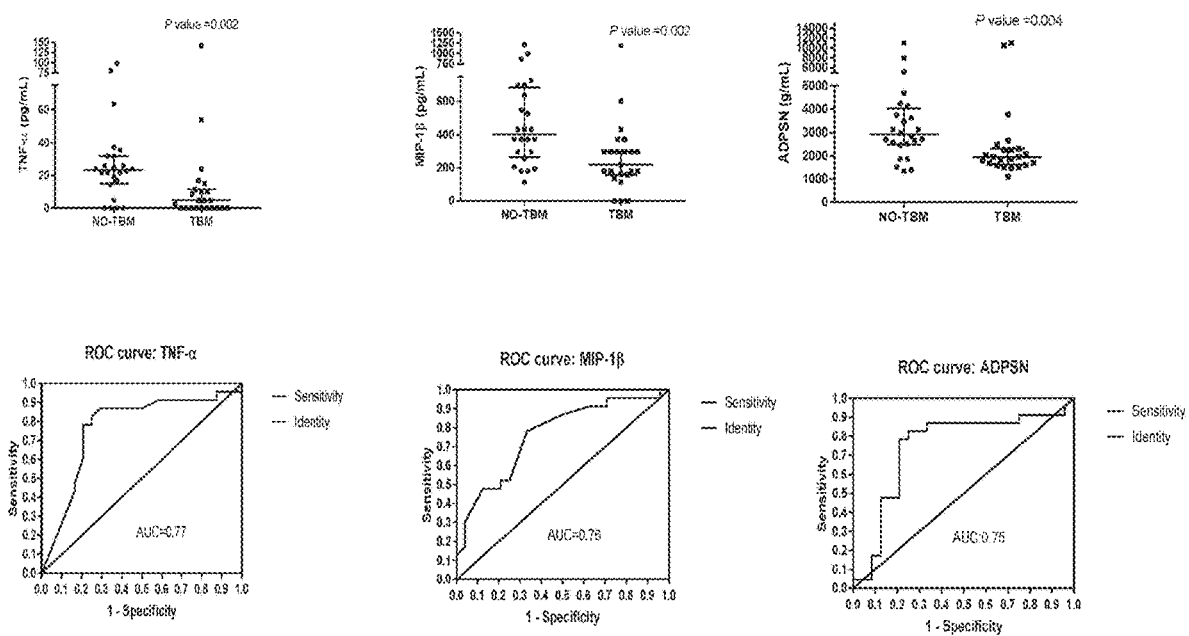
FIG. 4B: Representative plots showing the levels of biomarkers detected in serum samples from children with TBM vs those without TBM and receiver operator characteristics (ROC) curves showing the accuracies of these biomarkers in the diagnosis of TB meningitis. Error bars in the scatter-dot plots indicate the median and inter-quartile ranges. Representative plots for six analytes with AUC≥0.75 are shown.

Potential of Individual Blood-Based Biomarkers in the Diagnosis of TB Meningitis Out of the markers that were investigated, the median serum levels of 18 including sVCAM1, CCL2, IL_4, TNF-α, CCL4, adipsin, SAP, CC5, CFH, G-CSF, IL-10, Apo-CIII, IL-17A, PAI-1 (total), PDGF AB/BB, MBL and NCAM1 were significantly different (p<0.05) between the children with or without TBM according to the Mann Whitney U test, with the levels of five (CC4b, MMP-1, CXCL8, CC4, sRAGE) showing trends (0.05<p≤0.09). When the diagnostic potentials of individual serum biomarkers were assessed by ROC curve analysis, 21 of the markers showed promise, as ascertained by AUC 0.65 (VCAM-1, MCP-1/CCL2, IL-4, TNF-α, MIP-1β/CCL4, ADPSN/CFD, SAP, CC5, CFH, G-CSF, IL-10, Apo CIII, IL-17A, PAI-1, PDGF-AB/BB, MBL, NCAM-1, CC4b, MMP-1, CXCL8/IL-8, CC4) (Table 3, FIG. 4).

TABLE 3

Median levels of host markers detected in serum samples from children with TBM or no-TBM disease (Inter-quartile range in parenthesis) and accuracies in the diagnosis TBM. The data shown are raw, untransformed values. Cut-off values and associated sensitivities and specificities were selected based on the Youden's index.

| Markers | Median in TBM (IQR) | Median in No-TBM (IQR) | p-value | AUC (95% CI) | Cut-off Value | Sensitivity % (95% CI) | Specificity % (95% CI) |
|---|---|---|---|---|---|---|---|
| VCAM-1 | 1197300.0 (952940.0-1543500.0) | 1802000.0 (1456400.0-2521350.0) | 0.000188 | 0.82 (0.70-0.94) | <1580000.0 | 78.3 (56.3-92.5) | 66.7 (44.7-84.4) |
| MCP-1/CCL2 | 244.3 (165.5-390.9) | 512.3 (319.7-994.8) | 0.000262 | 0.81 (0.69-0.93) | <327.3 | 73.9 (51.6-89.7) | 75.0 (53.3-90.2) |
| IL-4 | 82.7 (7.42-99.6) | 136.8 (99.6-191.3) | 0.001147 | 0.78 (0.65-0.91) | <116.7 | 78.3 (56.3-92.5) | 62.5 (40.6-81.2) |
| TNF-α | 4.8 (0.0-11.4) | 23.3 (15.7-31.9) | 0.001457 | 0.77 (0.62-0.91) | <12.9 | 78.3 (56.3-92.5) | 79.2 (57.9-92.9) |

TABLE 3-continued

Median levels of host markers detected in serum samples from children with TBM or no-TBM disease (Inter-quartile range in parenthesis) and accuracies in the diagnosis TBM. The data shown are raw, untransformed values. Cut-off values and associated sensitivities and specificities were selected based on the Youden's index.

| Markers | Median in TBM (IQR) | Median in No-TBM (IQR) | p-value | AUC (95% CI) | Cut-off Value | Sensitivity % (95% CI) | Specificity % (95% CI) |
|---|---|---|---|---|---|---|---|
| MIP-1β/CCL4 | 219.0 (158.1-296.8) | 401.4 (275.7-667.2) | 0.002148 | 0.76 (0.62-0.90) | <334.3 | 78.3 (56.3-92.5) | 66.7 (44.7-84.4) |
| ADPSN/CFD | 1950.4 (1611.1-2319.1) | 2917.4 (2493.4-3938.5) | 0.004065 | 0.75 (0.59-0.90) | <2393.0 | 78.3 (56.3-92.5) | 79.2 (57.9-92.9) |
| SAP | 331539.9 (261542.1-655100.2) | 167660.5 (88309.6-286067.7) | 0.005664 | 0.74 (0.59-0.89) | >257478.0 | 78.3 (56.3-92.5) | 70.8 (48.9-87.4) |
| CC5 | 52307.0 (44989.9-59967.4) | 38538.0 (28210.6-47089.8) | 0.006660 | 0.73 (0.58-0.88) | >46742.0 | 69.6 (47.1-86.8) | 75.0 (53.3-90.2) |
| CFH | 415846.5 (363515.9-470137.5) | 314294.0 (261691.8-412727.7) | 0.009719 | 0.72 (0.57-0.87) | >350185.0 | 87.0 (66.4-97.2) | 66.7 (44.7-84.4) |
| G-CSF | 14.0 (0.0-117.6) | 147.6 (25.1-463.4) | 0.010573 | 0.72 (0.57-0.86) | <76.0 | 65.2 (42.7-83.6) | 70.8 (48.9-87.4) |
| IL-10 | 0.0 (0.0-4.1) | 8.1 (0.0-21.2) | 0.011193 | 0.70 (0.56-0.85) | <7.0 | 95.7 (78.1-99.9) | 54.2 (32.8-74.5) |
| Apo CIII | 151289.3 (130100.8-181642.4) | 95825.1 (63481.7-161543.8) | 0.014822 | 0.71 (0.55-0.87) | >114926.0 | 87.0 (66.4-97.2) | 62.5 (40.6-81.2) |
| IL-17A | 0.0 (0.0-0.0) | 0.0 (0.0-18.4) | 0.018640 | 0.65 (0.53-0.76) | <11.3 | 95.7 (78.1-99.9) | 37.5 (18.8-59.4) |
| PAI-1 | 348736.6 (261199.3-456794.4) | 246289.2 (175941.2-350988.5) | 0.018694 | 0.70 (0.55-0.85) | >255621.0 | 78.3 (56.3-92.5) | 58.3 (36.6-77.9) |
| PDGF-AB/BB | 49576.6 (33649.3-83528.9) | 33592.0 (14786.0-49751.6) | 0.032444 | 0.68 (0.53-0.84) | >42307.0 | 65.2 (42.7-83.6) | 66.7 (44.7-84.4) |
| MBL | 9533.4 (4686.1-30439.6) | 3299.1 (901.1-14882.4) | 0.033928 | 0.68 (0.52-0.84) | >4522.0 | 78.3 (56.3-92.5) | 58.3 (36.6-77.9) |
| NCAM-1 | 246692.5 (164329.5-305706.5) | 285446.4 (256271.6-342048.0) | 0.036064 | 0.68 (0.52-0.84) | <264419.0 | 69.6 (47.1-86.8) | 70.8 (48.9-87.4) |
| CC4b | 29843.2 (21128.5-42752.7) | 25562.6 (17752.8-31264.4) | 0.056822 | 0.66 (0.51-0.82) | >26285.0 | 69.6 (47.1-86.8) | 54.2 (32.8-74.5) |
| MMP-1 | 5694.6 (3233.2-7609.0) | 4084.8 (2174.5-6345.7) | 0.068827 | 0.66 (0.50-0.81) | >4282.0 | 60.9 (38.5-80.3) | 54.2 (32.8-74.5) |
| CXCL8/IL-8 | 37.1 (15.5-54.1) | 55.4 (27.5-112.9) | 0.072101 | 0.65 (0.49-0.81) | <42.1 | 60.9 (38.5-80.3) | 66.7 (44.7-84.4) |
| CC4 | 157528.9 (90929.3-209684.1) | 85388.5 (48405.5-194821.2) | 0.079129 | 0.65 (0.49-0.81) | >89484.0 | 78.3 (56.3-92.5) | 54.2 (32.8-74.5) |
| sRAGE | 855.2 (773.7-896.6) | 875.8 (855.2-937.8) | 0.094181 | 0.64 (0.48-0.80) | <875.8 | 73.9 (51.6-89.8) | 50.0 (29.1-70.9) |
| TGF-α | 60.3 (26.9-96.2) | 28.5 (5.6-79.8) | 0.110002 | 0.64 (0.48-0.80) | >29.9 | 69.6 (47.1-86.8) | 54.2 (32.8-74.5) |
| IL-7 | 36.0 (22.9-55.8) | 29.2 (12.4-37.7) | 0.110363 | 0.64 (0.48-0.80) | >27.5 | 69.6 (47.1-86.8) | 50.0 (29.1-70.9) |
| NCAM | 409831.4 (339777.0-520833.0) | 454959.6 (390928.0-577059.4) | 0.133505 | 0.63 (0.47-0.79) | <444907.0 | 60.9 (38.5-80.3) | 58.3 (36.6-77.9) |
| IL-6 | 6.8 (1.6-14.6) | 8.9 (2.5-44.7) | 0.135692 | 0.63 (0.47-0.79) | <8.0 | 56.5 (34.5-76.8) | 58.3 (36.6-77.9) |
| GM-CSF | 0.0 (0.0-0.0) | 0.0 (0.0-0.0) | 0.158099 | 0.57 (0.40-0.73) | <9.3 | 100.0 (85.2-100) | 16.7 (4.7-37.4) |

TABLE 3-continued

Median levels of host markers detected in serum samples from children with TBM or no-TBM disease (Inter-quartile range in parenthesis) and accuracies in the diagnosis TBM. The data shown are raw, untransformed values. Cut-off values and associated sensitivities and specificities were selected based on the Youden's index.

| Markers | Median in TBM (IQR) | Median in No-TBM (IQR) | p-value | AUC (95% CI) | Cut-off Value | Sensitivity % (95% CI) | Specificity % (95% CI) |
|---|---|---|---|---|---|---|---|
| Apo AI | 302283.6 (267898.0-346446.2) | 286350.3 (191698.6-320139.9) | 0.160089 | 0.62 (0.46-0.78) | >287512.0 | 65.2 (42.7-83.6) | 54.2 (32.8-74.5) |
| VEGF-A | 152.4 (112.5-251.2) | 106.7 (74.8-235.8) | 0.169862 | 0.62 (0.45-0.78) | >111.2 | 78.3 (56.3-92.5) | 54.2 (32.8-74.5) |
| Aβ40 | 0.0 (0.0-0.0) | 0.0 (0.0-0.0) | 0.171006 | 0.54 (0.37-0.71) | <72.1 | 100.0 (85.2-100.0) | 8.3 (1.0-27.0) |
| CF1 | 66236.8 (49972.0-99204.5) | 54181.1 (45646.3-71882.7)) | 0.176578 | 0.62 (0.45-0.78) | >57835.0 | 65.2 (42.7-83.6) | 62.5 (40.6-81.2) |
| MMP-7 | 808.0 (524.4-1584.1) | 1175.0 (625.5-3399.8) | 0.189921 | 0.61 (0.45-0.78) | <869.0 | 60.9 (38.5-80.3) | 62.5 (40.6-81.2) |
| Myoglobin | 9.6 (4.4-20.3) | 21.4 (4.9-51.0) | 0.201135 | 0.61 (0.44-0.78) | <10.2 | 60.9 (38.5-80.3) | 66.7 (44.7-84.4) |
| CXCL10/IP-10 | 55.9 (35.9-169.1) | 75.8 (49.3-298.3) | 0.213146 | 0.61 (0.44-0.77) | <57.2 | 52.2 (30.6-73.2) | 66.7 (44.7-84.4) |
| PDGF-AA | 8538.7 (5683.1-15788.5) | 6995.0 (2635.5-12806.3) | 0.221073 | 0.61 (0.44-0.77) | >6150.0 | 69.6 (47.1-86.8) | 50.0 (29.1-70.9) |
| MIP4 | 241.6 (172.5-366.9) | 178.1 (119.2-342.3) | 0.221073 | 0.61 (0.44-0.77) | >187.7 | 69.6 (47.1-86.8) | 54.2 (32.8-74.5) |
| Aβ42 | 0.0 (0.0-0.0) | 0.0 (0.0-556.9) | 0.240593 | 0.58 (0.45-0.72) | <278.4 | 73.9 (51.6-89.8) | 41.7 (22.1-63.4) |
| CC3 | 40885.9 (36448.0-74127.5) | 46059.4 (25390.4-53871.9) | 0.254876 | 0.40 (0.23-0.57) | >32056.0 | 91.3 (72.0-98.9) | 41.7 (22.1-63.4) |
| A1AT | 18729.1 (14631.0-24621.2) | 16819.0 (11711.3-27780.9) | 0.287284 | 0.59 (0.42-0.76) | >17908.0 | 60.9 (38.5-80.3) | 58.3 (36.6-77.9) |
| P-Selectin | 194.3 (102.1-352.1) | 119.1 (54.4-274.0) | 0.330420 | 0.58 (0.42-0.75) | >159.1 | 65.2 (42.7-83.6) | 62.5 (40.6-81.2) |
| CC5a | 2663.1 (1751.2-3946.9) | 2423.2 (1559.1-3554.3) | 0.349063 | 0.58 (0.41-0.75) | >2660.0 | 52.2 (30.6-73.2) | 66.7 (44.7-84.4) |
| IL-12/23p40 | 0.0 (0.0-0.0) | 0.0 (0.0-0.0) | 0.349077 | 0.52 (0.35-0.69) | <620.1 | 100.0 (85.2-100.0) | 4.2 (0.1-21.1) |
| IL-1β | 0.0 (0.0-0.0) | 0.0 (0.0-9.2) | 0.358788 | 0.56 (0.43-0.68) | <8.3 | 91.3 (72.0-98.9) | 29.2 (12.6-51.1) |
| MMP-8 | 24763.5 (12747.3-86623.8) | 19342.7 (9257.2-35601.6) | 0.360001 | 0.59 (0.41-0.75) | >22769.0 | 56.5 (34.5-76.8) | 58.3 (36.6-77.9) |
| CRP | 230000.0 (230000.0-230000.0) | 230000.0 (63731.2-230000.0) | 0.380342 | 0.56 (0.43-0.69) | >80721.0 | 87.0 (66.4-97.2) | 33.3 (15.6-55.3) |
| CCL3/MIP-1β | 48.7 (0.0-65.1) | 49.8 (0.0-209.1) | 0.382647 | 0.57 (0.41-0.74) | <48.9 | 65.2 (42.7-83.6) | 54.2 (32.8-74.5) |
| MMP-9 | 205449.19 (59802.48-556493.88) | 174486.7 (73396.4-266465.9) | 0.387093 | 0.57 (0.40-0.74) | >189764.0 | 56.5 (34.5-76.8) | 58.3 (36.6-77.9) |
| IL-21 | 0.0 (0.0-0.0) | 0.0 (0.0-15.9) | 0.396732 | 0.55 (0.43-0.67) | <34.6 | 95.7 (78.1-99.9) | 20.8 (7.1-42.2) |
| Cathepsin D | 439708.5 (308272.3-728466.0) | 493856.4 (331662.9-959098.3) | 0.412583 | 0.57 (0.40-0.74) | <459422.0 | 60.9 (38.5-80.3) | 54.2 (32.8-74.5) |
| ICAM-1 | 216547.6 (137559.5-286618.4) | 215566.5 (171273.1-337326.2) | 0.418679 | 0.57 (0.40-0.72) | <224039.0 | 56.5 (34.5-76.8) | 50.0 (29.1-70.9) |

TABLE 3-continued

Median levels of host markers detected in serum samples from children with TBM or no-TBM disease (Inter-quartile range in parenthesis) and accuracies in the diagnosis TBM. The data shown are raw, untransformed values. Cut-off values and associated sensitivities and specificities were selected based on the Youden's index.

| Markers | Median in TBM (IQR) | Median in No-TBM (IQR) | p-value | AUC (95% CI) | Cut-off Value | Sensitivity % (95% CI) | Specificity % (95% CI) |
|---|---|---|---|---|---|---|---|
| CC9 | 3295.9 (2497.1-4084.6) | 3657.9 (2600.8-4489.9) | 0.475866 | 0.56 (0.39-0.73) | <3502.0 | 65.2 (42.7-83.6) | 58.3 (36.6-77.9) |
| MPO | 4746700.0 (1779300.0-6026200.0) | 3438600.0 (1669250.0-4934150.0) | 0.475891 | 0.56 (0.39-0.73) | >4650000.0 | 52.2 (30.6-73.2) | 70.8 (48.9-87.4) |
| CD40L | 11633.0 (8228.9-16525.6) | 10742.2 (6930.7-17042.3) | 0.475891 | 0.56 (0.39-0.73) | >11151.0 | 65.2 (42.7-83.6) | 54.2 (32.8-74.5) |
| GDF-15 | 1.0 (0.6-1.6) | 1.1 (0.6-3.1) | 0.501871 | 0.56 (0.39-0.73) | <1.1 | 60.9 (38.5-80.3) | 54.2 (32.8-74.5) |
| D-dimer | 9287.6 (1772.3-17900.1) | 9102.9 (3021.2-41007.9) | 0.550286 | 0.55 (0.38-0.72) | <9451.0 | 52.2 (30.6-73.2) | 50.0 (29.1-70.9) |
| sICAM-1 | 244.4 (127.8-325.3) | 228.5 (154.3-427.6) | 0.572517 | 0.55 (0.38-0.72) | <300.1 | 69.6 (47.1-86.8) | 41.7 (22.1-63.4) |
| BDNF | 15636.7 (10109.5-24406.5) | 18107.0 (8952.6-28946.9) | 0.572783 | 0.55 (0.38-0.72) | <17211.0 | 65.2 (42.7-83.6) | 54.2 (32.8-74.5) |
| CXCL9/MIG | 2309.5 (0.0-3311.4) | 1800.7 (0.0-3557.3) | 0.625319 | 0.54 (0.38-0.71) | >2114.0 | 52.2 (30.6-73.2) | 62.5 (40.6-81.2) |
| SAA | 65700.0 (847.0-230000.0) | 39439.7 (6551.9-226031.8) | 0.656243 | 0.54 (0.37-0.71) | >59894.0 | 56.5 (34.5-76.8) | 66.7 (44.7-84.4) |
| IL-13 | 0.0 (0.0-338.1) | 0.0 (0.0-756.3) | 0.681743 | 0.53 (0.38-0.69) | <74.6 | 56.5 (34.5-76.8) | 45.8 (25.6-67.2) |
| CC2 | 15903.9 (8706.0-31171.1) | 15768.9 (6992.3-49343.7) | 0.725481 | 0.53 (0.36-0.70) | <15990.0 | 52.2 (30.6-73.2) | 50.0 (29.1-70.9) |
| Ferritin | 52841.0 (14202.0-114067.7) | 62740.4 (16776.2-169542.0) | 0.740490 | 0.53 (0.36-0.70) | <56314.0 | 56.5 (34.5-76.8) | 58.3 (36.6-77.9) |
| PEDF | 21756.5 (18654.6-25542.3) | 21401.6 (18159.9-26348.1) | 0.765743 | 0.53 (0.36-0.70) | >21725.0 | 52.2 (30.6-73.2) | 54.2 (32.8-74.5) |
| MP0 (alternative kit) | 917.9 (226.0-2175.5) | 755.8 (362.3-1288.0) | 0.773117 | 0.53 (0.36-0.70) | >796.0 | 56.5 (34.5-76.8) | 54.2 (32.8-74.5) |
| RANTES | 108231.8 (53485.5-169473.6) | 92692.2 (39285.6-188178.1) | 0.790226 | 0.52 (0.35-0.69) | >99016.0 | 56.5 (34.5-76.8) | 54.2 (32.8-74.5) |
| ADMTS13 | 901.2 (545.3-1092.7) | 874.4 (600.0-1120.0) | 0.823096 | 0.52 (0.35-0.68) | <962.3 | 60.9 (38.5-80.3) | 45.8 (25.6-67.2) |
| NGAL | 394.1 (152.5-1046.1) | 380.5 (189.3-560.3) | 0.831299 | 0.52 (0.35-0.69) | >371.5 | 52.2 (30.6-73.2) | 50.0 (29.1-70.9) |
| CCL1/I-309 | 15.0 (8.6-33.4) | 15.2 (7.6-44.4) | 0.848035 | 0.52 (0.35-0.69) | <15.2 | 52.2 (30.6-73.2) | 50.0 (29.1-70.9) |
| GDNF | 136.3 (120.1-152.7) | 136.3 (136.3-152.7) | 0.921886 | 0.51 (0.34-0.67) | <140.4 | 52.2 (30.6-73.2) | 41.7 (22.1-63.4) |
| IFN-γ | 0.0 (0.0-0.0) | 0.0 (0.0-0.0) | 0.928917 | 0.51 (0.39-0.63) | <61.5 | 87.0 (66.4-92.2) | 20.8 (7.1-42.2) |
| Cathelicidin-LL37 | 0.5 (0.3-0.9) | 0.5 (0.3-0.9) | 0.974533 | 0.49 (0.31-0.66) | >0.4 | 60.9 (38.5-80.3) | 34.8 (16.4-57.3) |
| S100B | 2800.0 (2744.2-2800.0) | 2800.0 (2744.2-2800.0) | 0.986591 | 0.50 (0.34-0.66) | >2772.0 | 55.6 (30.8-78.5) | 40.0 (19.1-64.0) |

Figure 5:
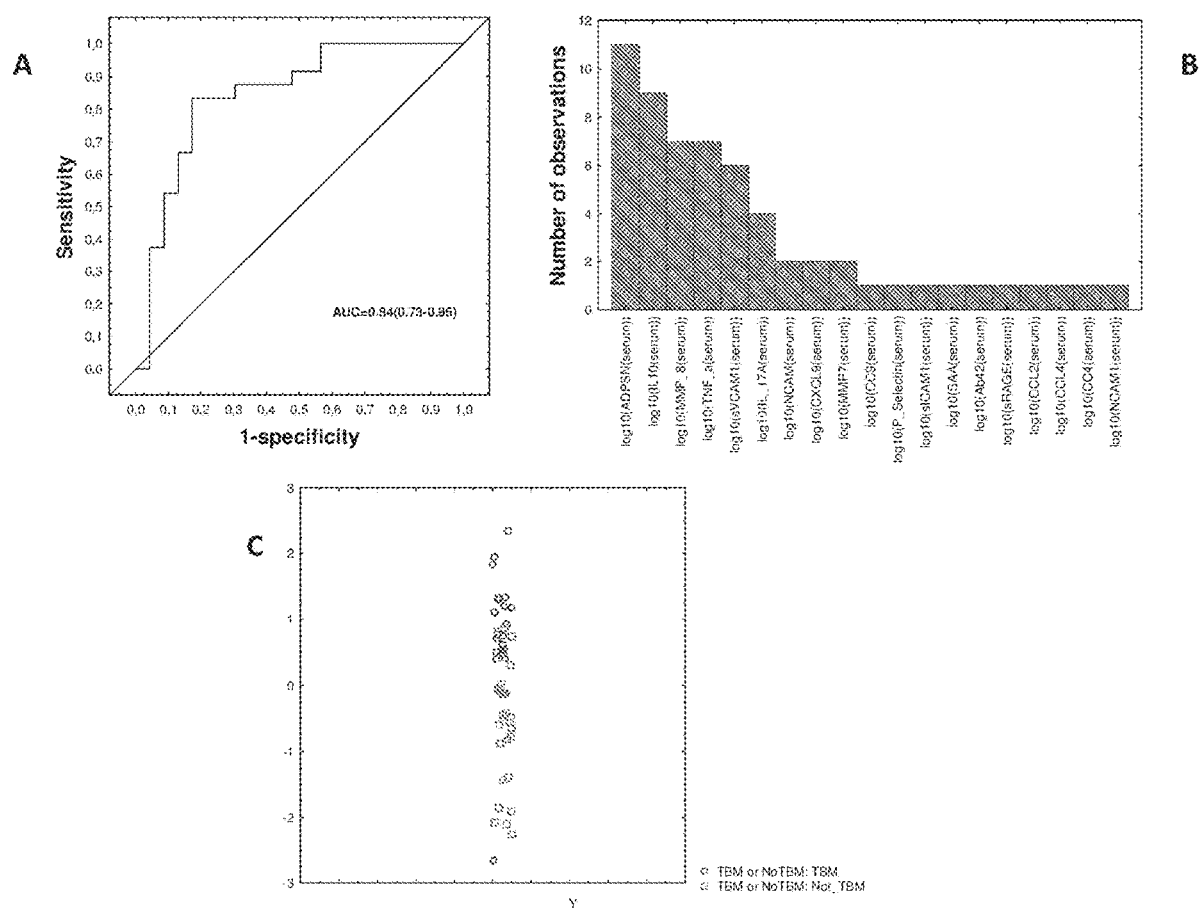
FIG. 5: Accuracy of a 3-marker serum biosignature (adipsin, Aβ42 and IL-10) in the diagnosis of TBM. ROC curve showing the accuracy of the three-marker biosignature (A), frequency of analytes in the top 11 GDA biosignatures that most accurately discriminated between TBM and no TBM disease (B), and scatter plot showing the ability of the 3-marker signature in classifying children as TBM or no TBM disease (C). The squares in C represent the children with no TBM and the circles represent the children with TBM.

Utility of Combinations of Analytes Detectable in Serum in the Diagnosis of TB Meningitis When the serum data obtained for all host markers were fitted to GDA models, optimal diagnosis of TBM was achieved when markers were used in combinations of three. The most accurate 3-marker serum biosignature for the diagnosis of TBM comprised adipsin (complement factor D), Aβ42 and IL-10 diagnosed TBM with an AUC of 0.84 (95% confidence interval, 0.73 to 0.96), corresponding to a sensitivity of 82.6% (19/23) and specificity of 75% (18/24). After leave-one-out cross validation, the sensitivity of the 3-marker serum biosignature remained 82.6% (19/23) with the specificity decreasing to 70.3% (17/24). However, further optimisation of the biosignature by selection of better cut-off values resulted in an improved sensitivity and specificity of 83% and 83%, respectively (FIG. 5).

DISCUSSION

The levels of 69 host biomarkers were evaluated in CSF and serum samples from children suspected of having TB meningitis. The findings included:
  i) identification of a novel four-marker CSF biosignature comprising MPO, sICAM-1, CXCL8 and IFN-γ, which diagnosed TBM disease with high accuracy (AUC of 0.97);
  ii) identification of a novel three-marker CSF biosignature comprising MPO, VEGF and IFN-γ and, which diagnosed TBM with high accuracy (AUC of 0.97);
  iii) identification of a novel three-marker blood-based biosignature comprising adipsin (complement factor D), Aβ42 and IL-10, which showed potential in the diagnosis of TBM (AUC of 0.84); and
  iv) identification of several candidate biomarkers that are detectable in CSF and serum samples from children with TBM and which showed strong potential as diagnostic candidates for the disease.

The Applicant is not aware of any existing CSF tests that perform with the high level of accuracy (specificity >95%) in the diagnosis of TBM.

None of the markers identified in the serum samples have been shown previously as potentially useful biomarkers for the diagnosis of TBM in children. An advantage of a blood-based test for the diagnosis of TBM is that such a test may be more easily applicable, especially in resource-limited settings. A blood-based test could make use of finger-prick blood, and such a test would be a major breakthrough in the diagnosis of TBM disease.

The biosignatures identified herein are not intended to be limited to diagnosing TBM in children, and it is also envisaged that these biosignatures could be used for diagnosing TBM in adults. The biosignatures can be used in point-of-care or bedside diagnosis tests and could be based on lateral flow technology.

In conclusion, four-marker and 3-marker CSF protein biosignatures have been identified which show strong potential to be used as diagnostic biosignatures for TBM. A 3-marker blood-based biosignature has also been identified. Point-of-care or bedside tests, based on the biosignatures identified herein, will lead to a significant improvement in the diagnosis of TBM, with a consequent reduction in the high morbidity and mortality that currently results from the late diagnosis of the disease.

Throughout the specification unless the content requires otherwise the word 'comprise' or variations such as 'comprises' or 'comprising' will be understood to imply the inclusion of a stated integer or group of integers but not the exclusion of any other integer or group of integers.

The invention claimed is:

1. A method for diagnosing and treating a subject with tuberculous meningitis (TBM), the method comprising the steps of:
    testing a cerebrospinal fluid (CSF) sample from a subject suspected of having TBM for the presence of MPO, IFN-γ and at least one other biomarker selected from the group consisting of SICAM-1, VEGF-A and CXCL8;
    determining that the subject has TBM based on the detection of the biomarkers in the sample; and
    administering an effective amount of TBM treatment to the subject.

2. The method according to claim 1, which comprises testing the CSF sample for MPO, IFN-γ and VEGF-A.

3. The method according to claim 1, which comprises testing the CSF sample for MPO, IFN-γ, SICAM-1 and CXCL8.

4. The method according to claim 1, which comprises additionally testing the CSF sample for one or more additional biomarkers selected from the group consisting of CCL18 (MIP-4), MIG (CXCL9), I-309 (CCL1), CCL5 (RANTES), IL-6, tumour necrosis factor (TNF)-α, matrix metalloproteinase (MMP)-9, MMP-8, complement C2 (CC2), total plasminogen activator inhibitor 1 (PAI-1), IL-1β, IP-10 (CXCL10), alpha-2-antitrypsin (A1AT), IL-10, granulocyte-macrophage colony stimulating factor (GM-CSF), CC4, CC4b, granulocyte colony stimulating factor (G-CSF), apolipoprotein (Apo)-A1, CC5a, platelet-derived growth factor (PDGF)-AB/BB, mannose-binding lectin (MBL), ferritin, CC5, serum amyloid P (SAP), complement factor H (CFH), P-Selectin, PDGF-AA, TGF-α, lipocalin-2 (NGAL), CC3, MIP-1β (CCL4), IL-17A, c-reactive protein (CRP), natural cell adhesion molecule (NCAM/CD56), CC9, CD40 ligand, complement factor 1 (CF1), MIP-1α (CCL3), D-dimer, Apo CIII, VCAM-1, IL-12/23p40, adipsin (Complement factor D), GDF-15, PEDF, MMP-1, serum amyloid A (SAA), amyloid beta-40 (Aβ40), ADMTS13, Aβ42, myoglobin, MCP-1 (CCL2), S100B, MMP-7, IL-4, sRAGE and cathepsin D.

5. The method according to claim 1, wherein the subject is a child.

6. The method according to claim 1, wherein a capture agent is used to bind each of the biomarkers.

7. The method according to claim 6, wherein one or more indicators are provided to indicate when binding of each of the capture agents and biomarkers occurs.

8. The method according to claim 1, wherein a measured signal which equates to a level of biomarker in the sample which is higher than a threshold level of the same biomarker is an indicator of TBM.

* * * * *